United States Patent
Salvemini et al.

(10) Patent No.: US 10,851,378 B2
(45) Date of Patent: Dec. 1, 2020

(54) METHODS OF TREATING PAIN USING ANTI-GPR160 ANTIBODIES

(71) Applicant: Saint Louis University, St. Louis, MO (US)

(72) Inventors: Daniela Salvemini, Chesterfield, MO (US); Gina L. C. Yosten, St. Louis, MO (US); Willis K. Samson, St. Louis, MO (US)

(73) Assignee: Saint Louis University, St. Louis, MO (US)

( * ) Notice: Subject to any disclaimer, the term of this patent is extended or adjusted under 35 U.S.C. 154(b) by 0 days.

(21) Appl. No.: 15/744,540

(22) PCT Filed: Jul. 15, 2016

(86) PCT No.: PCT/US2016/042473
§ 371 (c)(1),
(2) Date: Jan. 12, 2018

(87) PCT Pub. No.: WO2017/011738
PCT Pub. Date: Jan. 19, 2017

(65) Prior Publication Data
US 2018/0201938 A1  Jul. 19, 2018

Related U.S. Application Data

(60) Provisional application No. 62/193,306, filed on Jul. 16, 2015.

(51) Int. Cl.
| | | |
|---|---|---|
| A61K 39/395 | (2006.01) | |
| C07K 16/28 | (2006.01) | |
| C12N 15/113 | (2010.01) | |
| C07K 14/705 | (2006.01) | |
| G01N 33/566 | (2006.01) | |
| A61P 25/00 | (2006.01) | |
| A61P 29/00 | (2006.01) | |
| A61K 31/713 | (2006.01) | |
| A61K 38/17 | (2006.01) | |
| A61K 45/06 | (2006.01) | |
| A61K 39/00 | (2006.01) | |

(52) U.S. Cl.
CPC ........ *C12N 15/1138* (2013.01); *A61K 31/713* (2013.01); *A61K 38/1709* (2013.01); *A61K 45/06* (2013.01); *A61P 25/00* (2018.01); *A61P 29/00* (2018.01); *C07K 14/705* (2013.01); *C07K 16/28* (2013.01); *G01N 33/566* (2013.01); *A61K 2039/505* (2013.01); *C07K 2317/76* (2013.01); *C12N 2310/14* (2013.01)

(58) Field of Classification Search
None
See application file for complete search history.

*Primary Examiner* — Christine J Saoud
*Assistant Examiner* — Jon M Lockard
(74) *Attorney, Agent, or Firm* — Stinson LLP

(57) ABSTRACT

The disclosure provides methods and compositions for inhibiting pain by administering a GPR160 antagonist to a subject in need thereof. Also provided are methods of using GPR160 antagonists in combination with other pain therapies.

21 Claims, 7 Drawing Sheets

Specification includes a Sequence Listing.

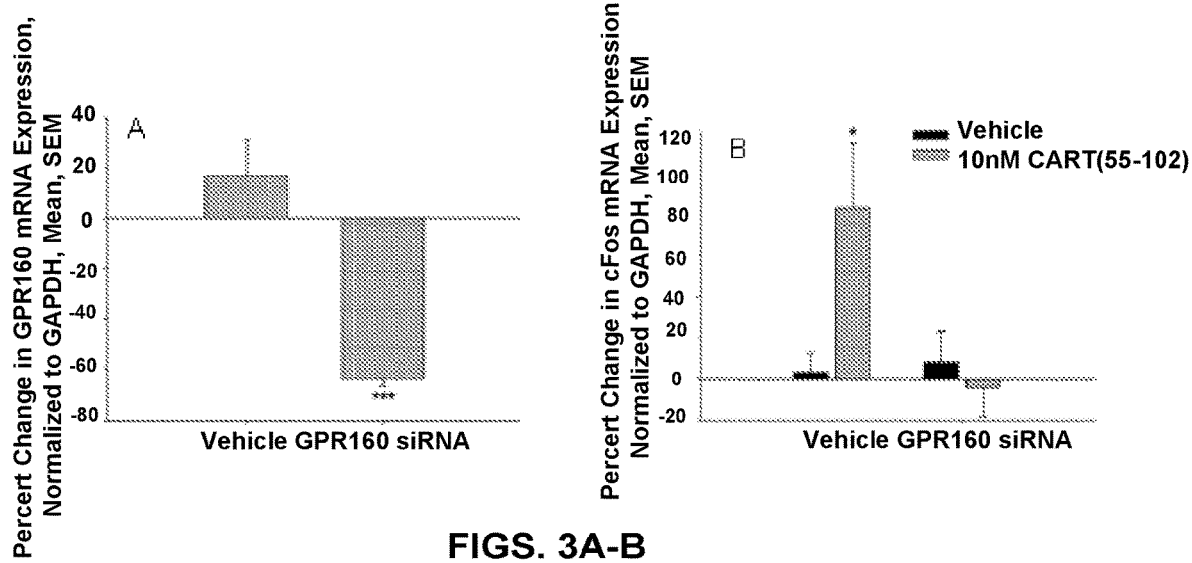
FIGS. 3A-B
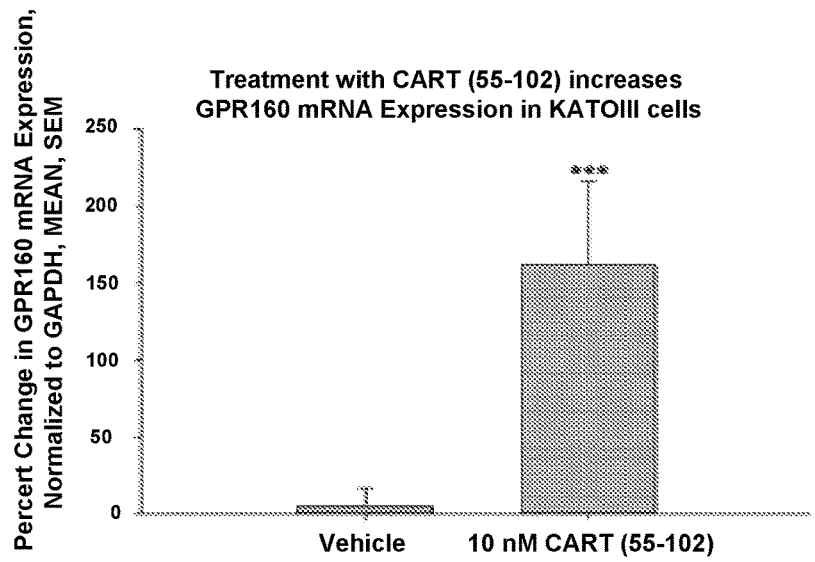
FIG. 4

METHODS OF TREATING PAIN USING ANTI-GPR160 ANTIBODIES

This application is a national phase application under 35 U.S.C. § 371 of International Application No. PCT/US2016/042473, filed Jul. 15, 2016, which claims benefit of priority to U.S. Provisional Application Ser. No. 62/193,306, filed Jul. 16, 2015, the entire contents of each of which are hereby incorporated by reference.

BACKGROUND

1. Field

This disclosure relates to the fields of medicine and cell biology. More specifically, it relates to the use of GPR160 antagonists to treat pain, either as a stand alone therapeutic option, or in combination with other pain therapies.

2. Related Art

A devastating health problem in the United States is the inadequate treatment of pain. One third of all Americans suffer from some form of chronic pain, and a third of these have pain, which is resistant to current medical therapy. The economic impact of pain is equally large at approximately $100 billion annually (Renfry, 2003). Opioid/narcotic analgesics, typified by morphine, are the most effective treatments for acute and chronic severe pain. However, their clinical utility is often hampered by the development of analgesic tolerance which requires escalating doses to achieve equivalent pain relief (Foley, 1995). This complex pathophysiological cycle represents a critical barrier to the quality of life of these patients due to the resulting drug-induced sedation, reduced physical activity, constipation, respiratory depression, high potential for addiction, and other side-effects (Foley, 1995). Accordingly, there is major interest in new approaches to treat chronic pain without engendering tolerance or unacceptable side-effects.

SUMMARY

Thus, in accordance with the present disclosure, there is provided a method of treating pain in a subject comprising administering to said subject an amount of a GPR160 antagonist sufficient to treat pain. The antagonist may be an interfering RNA, an antisense molecule, an antibody, a small molecule or a fragment of cocaine and amphetamine regulated transcript (CART) that binds but does not activate GPR160. The subject may be a human, or a non-human mammal. The pain may be chronic pain, acute pain and/or neuropathic pain.

The antagonist may be administered with a second anti-pain agent. The antagonist and said second anti-pain agent may be co-formulated. If not co-formulated, the antagonist and said second anti-pain agent may be delivered at distinct times, such as where the antagonist is delivered before said second anti-pain agent, or after said second anti-pain agent. The antagonist and said second anti-pain agent may be delivered in alternating administrations. The second anti-pain agent may be an opioid or a gabapentanoid.

The antagonist may be delivered over a period of one week, two weeks, three weeks, four weeks, one month, two months, three months, four months, five months, six months, seven months, eight months, nine months, ten months, eleven months, one year, two years or three years. The antagonist may be delivered by continuous infusion, such as by an implanted pump. The pain may be the result of an injury, such as a penetration wound, a burn, frostbite or a fracture, or as the result of a disease, such as diabetes, post-surgical pain, cancer, spinal nerve disease, multiple sclerosis, arthritis, an autoimmune disease, or an infection.

It is contemplated that any method or composition described herein can be implemented with respect to any other method or composition described herein. The use of the word "a" or "an" when used in conjunction with the term "comprising" in the claims and/or the specification may mean "one," but it is also consistent with the meaning of "one or more," "at least one," and "one or more than one." The word "about" means plus or minus 5% of the stated number.

Other objects, features and advantages of the present disclosure will become apparent from the following detailed description. It should be understood, however, that the detailed description and the specific examples, while indicating specific embodiments of the disclosure, are given by way of illustration only, since various changes and modifications within the spirit and scope of the disclosure will become apparent to those skilled in the art from this detailed description.

BRIEF DESCRIPTION OF THE FIGURES

The following drawings form part of the present specification and are included to further demonstrate certain aspects of the present disclosure. The disclosure may be better understood by reference to one or more of these drawings in combination with the detailed.

FIGS. 3A-B. Knockdown of GPR160 inhibits CART-induced cFos mRNA expression in KATOIII cells. (FIG. 3A) Knockdown of GPR160. (FIG. 3B) Expression of cFos mRNA in cells transfected with vehicle (Lipofectamine 2000 alone) or GPR160 siRNA prior to exposure to either vehicle (serum-free media) or 10 nM CART (55-102).

FIG. 4. Treatment with CART (55-102) leads to induction of GPR160 mRNA expression in KATOIII cells, as determined by qPCR.

DESCRIPTION OF ILLUSTRATIVE EMBODIMENTS

Figure 1:
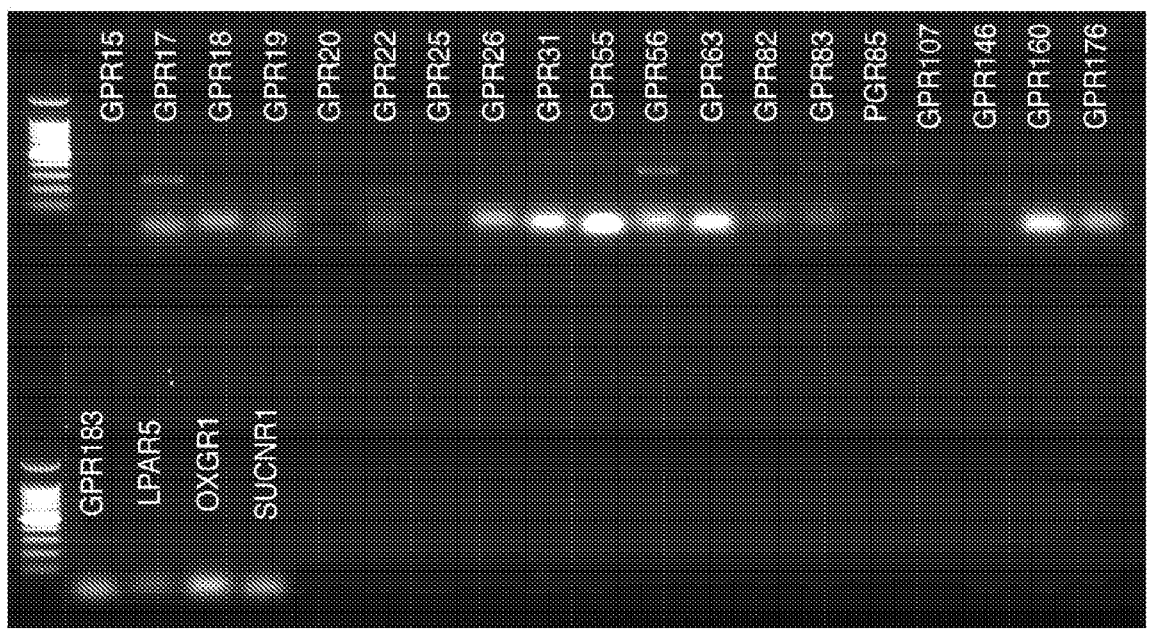
FIG. 1. Expression of Orphan GPCRs in normal rat dorsal horn, as determined by PCR.

G protein coupled receptors (GPCRs) are the most abundant receptor family encoded by the human genome and are involved in regulating a diverse array of cellular functions, including neurotransmission, cell growth, adhesion, and mobility. GPCRs are categorized based on homology and grouped into one of six classes (Class A-F), with most receptors that bind to small peptide hormones falling into Class A. Of the approximately 400 non-sensory GPCRs, ~120 receptors are considered "orphans," as their cognate ligands have not yet been identified (Alexander et al., 2013).

In order to identify orphan GPCRs that might be involved in mediating neuropathic pain, the inventors first used NCBI BLAST (database: RefSeq; algorithm: blastn) to compare the sequences of GPCRs known to play a role in pain transmission (Table 1) to orphan GPCRs, since similarity in sequence may indicate similarity in function. Orphan GPCRs exhibiting an E value of less than 10 were considered significant matches, and were considered for further analyses (Table 1).

TABLE 1

GPCRs Involved in Mediating Pain Responses, and Orphan GPCRs Bearing Significant Homology to those GPCRs

GPCRs Known to Mediate Pain Responses

| 5-HT | Muscarinic | Adenosine | Angiotensin | Apelin | Bombesin | Bradykinin | Cannabinoid | Chemokine Receptors | CCK |
|---|---|---|---|---|---|---|---|---|---|
| Dopamine | Galinin | Histamine | Leukotiene | Lyso-phospholipd | Neuropeptide FF | NPY | NPW | Opioid | P2X/P2Y |
| SST | Substance P | Neuromedin U | NPS | Neurotensin | Tachykinin | Prostanoid | Oxytocin | S1P | Proteinase-Activated Peptide |

Orphan GPCRs with Significant Homology to GPCRs Involved in Pain

| GPR3 | GPR15 | GPR17 | GPR18 | GPR19 | GPR20 | GPR22 | GPR25 | GPR26 | GPR30 |
|---|---|---|---|---|---|---|---|---|---|
| GPR31 | GPR35 | GPR45 | GPR55 | GPR56 | GPR63 | GPR68 | GPR82 | GPR83 | GPR85 |
| GPR107 | GPR146 | GPR151 | GPR152 | GPR160 | GPR174 | GPR176 | GPR182 | GPR183 | CMKLR1 |
| LPAR5 | MAS1 | MRGPRX1 | OXGR1 | SUCNR1 | TAAR2 | TAAR5 | TAAR9 | | |

Using an in vitro model system, the inventors have found that siRNA knockdown of GPR160, a previously orphaned G protein coupled receptor (GPCR) that is highly conserved across multiple species, including mouse, rat, and human, ablates cocaine- and amphetamine-regulated transcript (CART)-induced signaling (i.e., cFos mRNA expression, as determined by quantitative PCR). This suggests that GPR160 is a receptor for CART. GPR160 mRNA expression is dramatically elevated in a model of neuropathic pain (percent increase=~200%), and CART administration has been shown by others to enhance pain perception.

The inventors therefore tested whether knockdown of GPR160 could diminish pain perception in rats. Indeed, siRNA directed against GPR160 injected into the dorsal horn not only inhibited the development of chronic neuropathic pain in a well established rat model (chronic constriction injury) but also completely reversed it when given at time of peak neuropathic pain (day 7 post injury) without observable side effects or signs of sedation or lethargy.

Thus, the inventors propose that GPR160 is a receptor for CART, and that antagonists of GPR160 can be used for the treatment of neuropathic pain, either as stand alone or in combination with currently used analgesics (e.g., opioids and gabapentanoids). Furthermore, these agents are also anticipated to be effective in the management of other pain states such as rheumatoid arthritis. These and other aspects of the disclosure are described in detail below.

I. PAIN

Pain is an unpleasant feeling often caused by intense or damaging stimuli. The International Association for the Study of Pain's widely used definition states: "Pain is an unpleasant sensory and emotional experience associated with actual or potential tissue damage, or described in terms of such damage."

Pain motivates the individual to withdraw from damaging situations, to protect a damaged body part while it heals, and to avoid similar experiences in the future. Most pain resolves promptly once the painful stimulus is removed and the body has healed, but sometimes pain persists despite removal of the stimulus and apparent healing of the body; and sometimes pain arises in the absence of any detectable stimulus, damage or disease.

Pain is the most common reason for physician consultation in the United States. It is a major symptom in many medical conditions, and can significantly interfere with a person's quality of life and general functioning. Psychological factors such as social support, hypnotic suggestion, excitement, or distraction can significantly modulate pain's intensity or unpleasantness.

The International Association for the Study of Pain (IASP) has classified pain according to specific characteristics: (a) region of the body involved (e.g., abdomen, lower limbs), (b) system whose dysfunction may be causing the pain (e.g., nervous, gastrointestinal), (c) duration and pattern of occurrence, (d) intensity and time since onset, and (e) etiology. This system has been criticized by Clifford J. Woolf and others as inadequate for guiding research and treatment. According to Woolf, there are three classes of pain: nociceptive pain (see hereunder), inflammatory pain which is associated with tissue damage and the infiltration of immune cells, and pathological pain which is a disease state caused by damage to the nervous system (neuropathic pain, see hereunder) or by its abnormal function (dysfunctional pain, like in fibromyalgia, irritable bowel syndrome, tension type headache, etc.).

A. Chronic Pain

Pain is usually transitory, lasting only until the noxious stimulus is removed or the underlying damage or pathology has healed, but some painful conditions, such as rheumatoid arthritis, peripheral neuropathy, cancer and idiopathic pain, may persist for years. Pain that lasts a long time is called chronic, and pain that resolves quickly is called acute. Traditionally, the distinction between acute and chronic pain has relied upon an arbitrary interval of time from onset; the two most commonly used markers being 3 months and 6 months since the onset of pain, though some theorists and researchers have placed the transition from acute to chronic pain at 12 months. Others apply acute to pain that lasts less than 30 days, chronic to pain of more than six months duration, and subacute to pain that lasts from one to six months. A popular alternative definition of chronic pain, involving no arbitrarily fixed durations is "pain that extends beyond the expected period of healing." Chronic pain may be classified as cancer pain or benign.

B. Nociceptive Pain

Nociceptive pain is caused by stimulation of peripheral nerve fibers that respond only to stimuli approaching or exceeding harmful intensity (nociceptors), and may be classified according to the mode of noxious stimulation; the most common categories being "thermal" (heat or cold), "mechanical" (crushing, tearing, etc.) and "chemical" (iodine in a cut, chili powder in the eyes). As subset of nocicipetive pain is called "inflammatory" pain, as it results from tissue damage and the response of innate inflammatory responses. Nociceptive pain may also be divided into "visceral," "deep somatic" and "superficial somatic" pain. Visceral structures are highly sensitive to stretch, ischemia and inflammation, but relatively insensitive to other stimuli that normally evoke pain in other structures, such as burning and cutting. Visceral pain is diffuse, difficult to locate and often referred to a distant, usually superficial, structure. It may be accompanied by nausea and vomiting and may be described as sickening, deep, squeezing, and dull. Deep somatic pain is initiated by stimulation of nociceptors in ligaments, tendons, bones, blood vessels, fasciae and muscles, and is dull, aching, poorly localized pain. Examples include sprains and broken bones. Superficial pain is initiated by activation of nociceptors in the skin or other superficial tissue, and is sharp, well-defined and clearly located. Examples of injuries that produce superficial somatic pain include minor wounds and minor (first degree) burns.

C. Neuropathic Pain

Neuropathic pain is pain caused by damage or disease that affects the somatosensory system. It may be associated with abnormal sensations called dysesthesia, and pain produced by normally non-painful stimuli (allodynia). Neuropathic pain may have continuous and/or episodic (paroxysmal) components. The latter are likened to an electric shock. Common qualities include burning or coldness, "pins and needles" sensations, numbness and itching. Nociceptive pain, by contrast, is more commonly described as aching.

Neuropathic pain may result from disorders of the peripheral nervous system or the central nervous system (brain and spinal cord). Thus, neuropathic pain may be divided into peripheral neuropathic pain, central neuropathic pain, or mixed (peripheral and central) neuropathic pain. Central neuropathic pain is found in spinal cord injury, multiple sclerosis, and some strokes. Aside from diabetes (see diabetic neuropathy) and other metabolic conditions, the common causes of painful peripheral neuropathies are herpes zoster infection, HIV-related neuropathies, nutritional deficiencies, toxins, remote manifestations of malignancies, immune mediated disorders and physical trauma to a nerve trunk.

Neuropathic pain is common in cancer as a direct result of cancer on peripheral nerves (e.g., compression by a tumor), or as a side effect of chemotherapy, radiation injury or surgery. After a peripheral nerve lesion, aberrant regeneration may occur. Neurons become unusually sensitive and develop spontaneous pathological activity, abnormal excitability, and heightened sensitivity to chemical, thermal and mechanical stimuli. This phenomenon is called "peripheral sensitization."

The (spinal cord) dorsal horn neurons give rise to the spinothalamic tract (STT), which constitutes the major ascending nociceptive pathway. As a consequence of ongoing spontaneous activity arising in the periphery, STT neurons develop increased background activity, enlarged receptive fields and increased responses to afferent impulses, including normally innocuous tactile stimuli. This phenomenon is called central sensitization. Central sensitization is an important mechanism of persistent neuropathic pain.

Other mechanisms, however, may take place at the central level after peripheral nerve damage. The loss of afferent signals induces functional changes in dorsal horn neurons. A decrease in the large fiber input decreases activity of interneurons inhibiting nociceptive neurons, i.e., loss of afferent inhibition. Hypoactivity of the descending antinociceptive systems or loss of descending inhibition may be another factor. With loss of neuronal input (deafferentation) the STT neurons begin to fire spontaneously, a phenomenon designated "deafferentation hypersensitivity." Neuroglia ("glial cells") may play a role in central sensitization. Peripheral nerve injury induces glia to release proinflammatory cytokines and glutamate—which, in turn influence neurons.

II. GPR160

Probable G-protein coupled receptor 160 is a protein that in humans is encoded by the GPR160 gene. The human protein sequence can be found at NP_055188, and the human mRNA sequence is at NM_014373.

The sequence for human GPR160 is as follows:

MTALSSENCSFQYQLRQTNQPLDVNYLLFLIILGKILLNILTLGMRRKN

TCQNFMEYFCISLAFVDLLLLVNISIILYFRDFVLLSIRFTKYHICLFTQ

IISFTYGFLHYPVFLTACIDYCLNFSKTTKLSFKCQKLFYFFTVILIWIS

VLAYVLGDPAIYQSLKAQNAYSRHCPFYVSIQSYWLSFFMVMILFVAFIT

CWEEVTTLVQAIRITSYMNETILYFPFSSHSSYTVRSKKIFLSKLIVCFL

STWLPFVLLQVIIVLLKVQIPAYIEMNIPWLYFVNSFLIATVYWFNCHK

LNLKDIGLPLDPFVNWKCCFIPLTIPNLEQIEKPISIMIC

III. CART

Cocaine and amphetamine regulated transcript, also known as CART, is a protein that in humans is encoded by the CARTPT gene. CART appears to have roles in reward, feeding, and stress, and it has the functional properties of an endogenous psychostimulant.

CART is a neuropeptide that produces similar behaviour in animals to cocaine and amphetamine, but conversely blocks the effects of cocaine when they are co-administered. The peptide is found in several areas, among them the ventral tegmental area (VTA) of the brain. When CART is injected into rat VTA, increased locomotor activity is seen, which is one of the signs of "central stimulation" caused by substances such as cocaine and amphetamine. The rats also tended to return to the place where they had been injected. This is called conditioned place preference and is seen after injection of cocaine.

CART peptides, in particular, CART (55-102), seem to have an important function in the regulation of energy homeostasis, and interact with several central appetite circuits. CART expression is regulated by several peripheral peptide hormones involved in appetite regulation, including leptin, cholecystokinin and ghrelin, with CART and cholecystokinin having synergistic effects on appetite regulation.

CART is released in response to repeated dopamine release in the nucleus accumbens, and may regulate the activity of neurons in this area. CART production is upregulated by CREB, a protein thought to be involved with the development of drug addiction, and CART may be an important therapeutic target in the treatment of stimulant abuse.

CART is an anorectic peptide and is widely expressed in both the central and peripheral nervous systems, particularly concentrated in the hypothalamus. CART is outside of the nervous system also expressed in pituitary endocrine cells, adrenomedullary cells, islet somatostatin cells, and in rat antral gastrin cells.

Studies of CART (54-102) action in rat lateral ventricle and amygdala suggest that CART play a role in anxiety-like behavior, induced by ethanol withdrawal in rats. Studies on CART knock-out mice indicates that CART modulates the locomotor, conditioned place preference and cocaine self-administration effect of psychostimulants. This suggests a positive neuromodulatory action of CART on psychostimulants effect on rat. CART is altered in the ventral tegmental area of cocaine overdose victims, and a mutation in the CART gene associates with alcoholism. CART peptides are inhibitors of food intake (anorexigenic) and closely associated with leptin and neuropeptide Y, two important food intake regulators. CART hypoactivity in the hypothalamus of depressed animals is associated with hyperphagia and weight gain. CART peptides are also involved in fear and startle behavior. CART is thought to play a key role in the opioid mesolimbic dopamine circuit that modulates natural reward processes.

CART was found by examining changes in the brain following cocaine or amphetamine administration. CART mRNA increased with cocaine administration. One of the goals was to find an endogenous anorexigenic substance. CART inhibited rat food intake by as much as 30 percent. When naturally-occurring CART peptides were blocked by means of injecting antibodies to CART, feeding increased. This led to suggestions that CART may play a role—though not being the only peptide—in satiety. By the end of the 1980's, researchers started to synthesize cocaine-like and CART-like-acting substances in order to find medications that could affect eating disorders as well as cocaine abuse. These cocaine-like substances are called phenyltropanes.

IV. PHARMACEUTICAL FORMULATIONS AND ROUTES OF ADMINISTRATION

A. GPR160 Antagonists

Antagonists of GPR160 will find use in the therapeutic methods described below. The antagonist may be a protein, a nucleic acid or a small molecule. Protein antagonists and nucleic acid antagonists are described in some detail below.

1. Protein Antagonists

In one embodiment, the antagonist of GPR160 may be a proteinaceous antagonist. Proteinaceous antagonists generally fall into two categories—antibodies that bind to the receptor, or protein fragments of the ligand, i.e., CART, that retain to ability to bind the receptor but fail to activate it as the normal ligand would the same.

Antibodies according to the present disclosure may be defined, in the first instance, by their binding specificity, which in this case is for GPR160. Those of skill in the art, by assessing the binding specificity/affinity of a given antibody using techniques well known to those of skill in the art, can determine whether such antibodies fall within the scope of the instant claims. U.S. Patent Publication 2011/0135570 discloses anti-GPR160 antibodies and is incorporated herein by reference.

In various embodiments, one may choose to engineer sequences of the identified antibodies for a variety of reasons, such as improved expression, improved cross-reactivity or diminished off-target binding.

Antibody molecules also comprise antibody fragments (such as F(ab'), F(ab')$_2$) that are produced, for example, by the proteolytic cleavage of the mAbs, or single-chain immunoglobulins producible, for example, via recombinant means. Such antibody derivatives are monovalent. In one embodiment, such fragments can be combined with one another, or with other antibody fragments or receptor ligands to form "chimeric" binding molecules. Significantly, such chimeric molecules may contain substituents capable of binding to different epitopes of the same molecule.

In related embodiments, the antibody is a derivative of the disclosed antibodies, e.g., an antibody comprising the CDR sequences identical to those in the disclosed antibodies (e.g., a chimeric, or CDR-grafted antibody). Alternatively, one may wish to make modifications, such as introducing conservative changes into an antibody molecule. In making such changes, the hydropathic index of amino acids may be considered. It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

The present disclosure also contemplates isotype modification. By modifying the Fc region to have a different isotype, different functionalities can be achieved. For example, changing to IgG$_1$ can increase antibody dependent cell cytotoxicity, switching to class A can improve tissue distribution, and switching to class M can improve valency.

Modified antibodies may be made by any technique known to those of skill in the art, including expression through standard molecular biological techniques, or the chemical synthesis of polypeptides. Methods for recombinant expression are addressed elsewhere in this document.

A Single Chain Variable Fragment (scFv) is a fusion of the variable regions of the heavy and light chains of immunoglobulins, linked together with a short (usually serine, glycine) linker. This chimeric molecule retains the specificity of the original immunoglobulin, despite removal of the constant regions and the introduction of a linker peptide. This modification usually leaves the specificity unaltered. These molecules were created historically to facilitate phage display where it is highly convenient to express the antigen binding domain as a single peptide. Alternatively, scFv can be created directly from subcloned heavy and light chains derived from a hybridoma. Single chain variable fragments lack the constant Fc region found in complete antibody molecules, and thus, the common binding sites (e.g., protein A/G) used to purify antibodies. These fragments can often be purified/immobilized using Protein L since Protein L interacts with the variable region of kappa light chains.

The recombinant antibodies of the present disclosure may also involve sequences or moieties that permit dimerization or multimerization of the receptors. Such sequences include those derived from IgA, which permit formation of multimers in conjunction with the J-chain. Another multimerization domain is the Gal4 dimerization domain. In other embodiments, the chains may be modified with agents such as biotin/avidin, which permit the combination of two antibodies.

In a separate embodiment, a single-chain antibody can be created by joining receptor light and heavy chains using a non-peptide linker or chemical unit. Generally, the light and heavy chains will be produced in distinct cells, purified, and subsequently linked together in an appropriate fashion (i.e., the N-terminus of the heavy chain being attached to the C-terminus of the light chain via an appropriate chemical bridge).

CART peptide and polypeptide antagonist will generally comprise molecules of 15 to about 60 residues in length derived from the human sequence of SEQ ID NO:1:

MESSRVRLLPLLGAALLLMLPLLGTRAQEDAELQPRALDIYSAVDDA
SHEKELIEALQEVLKKLKSKRVPIYEKKYGQVPMCDAGEQCAVRKGA
RIGKLCDCPRGTSCNSFLLKCL

A particular length may be 39 or 48 residues, less than 50 residues, less than 40 residues, less than 30 residues, less than 25 residues, less than 20 residues, 15-50 residues, or 15-40 residues, including 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, or 60 consecutive residues of SEQ ID NO: 1. Alternatively, the peptides may have 90%, 95%, or more identity with fragments SEQ ID NO: 1. Accordingly, sequences that have between about between about 80% and about 90%, between about 91% and 95%, about 97%, 98% or about 99% of amino acids that are identical or functionally equivalent to the amino acids of SEQ ID NO: 1.

2. Nucleic Acid Antagonists

In another embodiment, the antagonist of GPR160 may be a nucleic acid antagonist. Such antagonists include antisense molecules, ribozyme and inhibitory oligonucleotides, often referred to as interfering RNAs (e.g., siRNAs, shRNAs, miRNAs). The latter rely on RNA interference (RNAi), a biological process in which RNA molecules inhibit gene expression, typically by causing the destruction of specific mRNA molecules. Two types of small ribonucleic acid (RNA) molecules—microRNA (miRNA) and small interfering RNA (siRNA)—are central to RNA interference. RNAs are the direct products of genes, and these small RNAs can bind to other specific messenger RNA (mRNA) molecules and either increase or decrease their activity, for example by preventing an mRNA from producing a protein. RNA interference has an important role in defending cells against parasitic nucleotide sequences—viruses and transposons. It also influences development.

The RNAi pathway is found in many eukaryotes, including animals, and is initiated by the enzyme Dicer, which cleaves long double-stranded RNA (dsRNA) molecules into short double stranded fragments of ~20 nucleotide siRNAs. Each siRNA is unwound into two single-stranded RNAs (ssRNAs), the passenger strand and the guide strand. The passenger strand is degraded and the guide strand is incorporated into the RNA-induced silencing complex (RISC). The most well-studied outcome is post-transcriptional gene silencing, which occurs when the guide strand pairs with a complementary sequence in a messenger RNA molecule and induces cleavage by Argonaute, the catalytic component of the RISC complex. In some organisms, this process spreads systemically, despite the initially limited molar concentrations of siRNA.

siRNAs. Small interfering RNA (siRNA), sometimes known as short interfering RNA or silencing RNA, is a class of double-stranded RNA molecules, 20-25 base pairs in length. siRNA plays many roles, but it is most notable in the RNA interference (RNAi) pathway, where it interferes with the expression of specific genes with complementary nucleotide sequences. siRNA functions by causing mRNA to be broken down after transcription, resulting in no translation. siRNA also acts in RNAi-related pathways, e.g., as an antiviral mechanism or in shaping the chromatin structure of a genome. The complexity of these pathways is only now being elucidated. siRNAs and their role in post-transcriptional gene silencing (PTGS) in plants were first discovered by David Baulcombe's group in 1999. Thomas Tuschl and colleagues soon reported that synthetic siRNAs could induce RNAi in mammalian cells.

siRNAs have a well-defined structure: a short (usually 20 to 24-bp) double-stranded RNA (dsRNA) with phosphorylated 5' ends and hydroxylated 3' ends with two overhanging nucleotides. The Dicer enzyme catalyzes production of siRNAs from long dsRNAs and small hairpin RNAs. siRNAs can also be introduced into cells by transfection. Since in principle any gene can be knocked down by a synthetic siRNA with a complementary sequence, siRNAs are an important tool for validating gene function and drug targeting in the post-genomic era.

shRNAs. A small hairpin RNA or short hairpin RNA (shRNA) is an artificial RNA molecule with a tight hairpin turn that can be used to silence target gene expression via RNA interference (RNAi). Expression of shRNA in cells is typically accomplished by delivery of plasmids or through viral or bacterial vectors. shRNA is an advantageous mediator of RNAi in that it has a relatively low rate of degradation and turnover. However, it requires use of an expression vector, which can pose safety concerns.

The promoter choice is essential to achieve robust shRNA expression. At first, polymerase III promoters such as U6 and H1 were used; however, these promoters lack spatial and temporal control. As such, there has been a shift to using polymerase II promoters to regulate shRNA expression.

Expression of shRNA in cells can be obtained by delivery of plasmids or through viral or bacterial vectors. Delivery of plasmids to cells through transfection to obtain shRNA expression can be accomplished using commercially available reagents in vitro. However, this method is not applicable in vivo and thus has limited utility.

Use of a bacterial vector to obtain shRNA expression in cells is a relatively recent approach. It builds off research showing that recombinant *Escherichia coli*, containing a plasmid with shRNA, fed to mice can knock-down target gene expression in the intestinal epithelium.

A variety of viral vectors can be used to obtain shRNA expression in cells including adeno-associated viruses (AAVs), adenoviruses, and lentiviruses. With adeno-associated viruses and adenoviruses, the genomes remain episomal. This is advantageous as insertional mutagenesis is avoided. It is disadvantageous in that the progeny of the cell will lose the virus quickly through cell division unless the cell divides very slowly. AAVs differ from adenoviruses in that the viral genes have been removed and they have diminished packing capacity. Lentiviruses integrate into sections of transcriptionally active chromatin and are thus passed on to progeny cells. With this approach there is increased risk of insertional mutagenesis; however, the risk can be reduced by using an integrase-deficient lentivirus.

Once the vector has integrated into the host genome, the shRNA is then transcribed in the nucleus by polymerase II or polymerase III depending on the promoter choice. This product mimics pri-microRNA (pri-miRNA) and is processed by Drosha. The resulting pre-shRNA is exported from the nucleus by Exportin 5. This product is then processed by Dicer and loaded into the RNA-induced silencing complex (RISC). The sense (passenger) strand is degraded. The antisense (guide) strand directs RISC to mRNA that has a complementary sequence. In the case of perfect complementarity, RISC cleaves the mRNA. In the case of imperfect complementarity, RISC represses translation of the mRNA. In both of these cases, the shRNA leads to target gene silencing.

miRNAs. A microRNA (abbreviated miRNA) is a small non-coding RNA molecule (containing about 22 nucleotides) found in plants, animals, and some viruses, which functions in RNA silencing and post-transcriptional regulation of gene expression. Encoded by eukaryotic nuclear DNA in plants and animals and by viral DNA in certain viruses whose genome is based on DNA, miRNAs function via base-pairing with complementary sequences within mRNA molecules. As a result, these mRNA molecules are silenced by one or more of the following processes: 1) cleavage of the mRNA strand into two pieces, 2) destabilization of the mRNA through shortening of its poly(A) tail, and 3) less efficient translation of the mRNA into proteins by ribosomes. miRNAs resemble the small interfering RNAs (siRNAs) of the RNA interference (RNAi) pathway, except miRNAs derive from regions of RNA transcripts that fold back on themselves to form short hairpins, whereas siRNAs derive from longer regions of double-stranded RNA. The human genome may encode over 1000 miRNAs, which are abundant in many mammalian cell types and appear to target about 60% of the genes of humans and other mammals.

miRNAs are well conserved in both plants and animals, and are thought to be a vital and evolutionarily ancient component of genetic regulation. While core components of the microRNA pathway are conserved between plants and animals, miRNA repertoires in the two kingdoms appear to have emerged independently with different primary modes of action. Plant miRNAs usually have near-perfect pairing with their mRNA targets, which induces gene repression through cleavage of the target transcripts. In contrast, animal miRNAs are able to recognize their target mRNAs by using as little as 6-8 nucleotides (the seed region) at the 5' end of the miRNA, which is not enough pairing to induce cleavage of the target mRNAs. Combinatorial regulation is a feature of miRNA regulation in animals. A given miRNA may have hundreds of different mRNA targets, and a given target might be regulated by multiple miRNAs.

The first miRNA was discovered in the early 1990s. However, miRNAs were not recognized as a distinct class of biological regulators until the early 2000s. Since then, miRNA research has revealed different sets of miRNAs expressed in different cell types and tissues and has revealed multiple roles for miRNAs in plant and animal development and in many other biological processes. Aberrant expression of miRNAs has been implicated in numerous disease states, and miRNA-based therapies are under investigation.

Estimates of the average number of unique messenger RNAs that are targets for repression by a typical microRNA vary, depending on the method used to make the estimate, but several approaches show that mammalian miRNAs can have many unique targets. For example, an analysis of the miRNAs highly conserved in vertebrate animals shows that each of these miRNAs has, on average, roughly 400 conserved targets. Likewise, experiments show that a single miRNA can reduce the stability of hundreds of unique messenger RNAs, and other experiments show that a single miRNA may repress the production of hundreds of proteins, but that this repression often is relatively mild (less than 2-fold).

B. Formulations and Routes

Where clinical applications in treating pain are contemplated, it will be necessary to prepare pharmaceutical compositions in a form appropriate for the intended application. Generally, this will entail preparing compositions that are essentially free of pyrogens, as well as other impurities that could be harmful to humans or animals.

One will generally desire to employ appropriate salts and buffers to render materials stable and allow for uptake by target cells. Aqueous compositions of the present disclosure comprise an effective amount of the vector to cells, dissolved or dispersed in a pharmaceutically acceptable carrier or aqueous medium. Such compositions also are referred to as inocula. The phrase "pharmaceutically or pharmacologically acceptable" refers to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the compositions of the present disclosure, its use in therapeutic compositions is contemplated. Supplementary active ingredients also can be incorporated into the compositions.

The active compositions of the present disclosure may include classic pharmaceutical preparations. Administration of these compositions according to the present disclosure will be via any common route so long as the target tissue is available via that route. Such routes include intravenous, oral, nasal, buccal, rectal, vaginal or topical route. Alternatively, administration may be by orthotopic, transdermal, intradermal, subcutaneous, intramuscular, intraperitoneal, intrathecal or intravenous injection. Such compositions would normally be administered as pharmaceutically acceptable compositions, described supra. Of particular interest is transdermal, intraperitoneal, intravenous or oral administration.

With regard to transdermal delivery, a patch is particularly contemplated. There are five main types of transdermal patches. In the Single-layer Drug-in-Adhesive, the adhesive layer of this system also contains the drug. In this type of patch the adhesive layer not only serves to adhere the various layers together, along with the entire system to the skin, but is also responsible for the releasing of the drug. The adhesive layer is surrounded by a temporary liner and a backing. In Multi-layer Drug-in-Adhesive, the multi-layer drug-in adhesive patch is similar to the single-layer system in that both adhesive layers are also responsible for the releasing of the drug. One of the layers is for immediate release of the drug and other layer is for control release of drug from the reservoir. The multi-layer system is different however that it adds another layer of drug-in-adhesive, usually separated by a membrane (but not in all cases). This patch also has a temporary liner-layer and a permanent backing.

Unlike the Single-layer and Multi-layer Drug-in-adhesive systems, the reservoir transdermal system has a separate drug layer. The drug layer is a liquid compartment containing a drug solution or suspension separated by the adhesive layer. This patch is also backed by the backing layer. In this type of system the rate of release is zero order.

The Matrix system has a drug layer of a semisolid matrix containing a drug solution or suspension. The adhesive layer in this patch surrounds the drug layer partially overlaying it. This is also known as a monolithic device.

In Vapor Patches, the adhesive layer not only serves to adhere the various layers together but also to release vapour. The vapor patches are new on the market and they release essential oils for up to 6 hours. Vapor patches release essential oils and are used in cases of decongestion mainly. Other vapor patches on the market are controller vapour patches that improve the quality of sleep. Vapor patches that reduce the quantity of cigarettes that one smokes in a month are also available on the market.

The active compounds may also be administered parenterally or intraperitoneally. Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

For oral administration the polypeptides of the present disclosure may be incorporated with excipients and used in the form of non-ingestible mouthwashes and dentifrices. A mouthwash may be prepared incorporating the active ingredient in the required amount in an appropriate solvent, such as a sodium borate solution (Dobell's Solution). Alternatively, the active ingredient may be incorporated into an antiseptic wash containing sodium borate, glycerin and potassium bicarbonate. The active ingredient may also be dispersed in dentifrices, including: gels, pastes, powders and slurries. The active ingredient may be added in a therapeutically effective amount to a paste dentifrice that may include water, binders, abrasives, flavoring agents, foaming agents, and humectants.

The compositions of the present disclosure may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Upon formulation, solutions will be administered in a manner compatible with the dosage formulation and in such amount as is therapeutically effective. The formulations are easily administered in a variety of dosage forms such as injectable solutions, drug release capsules and the like. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media, which can be employed, will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences," 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

C. Subjects

The methods of the disclosure can be applied to a wide range of species, e.g., humans, non-human primates (e.g., monkeys, baboons, or chimpanzees), horses, cattle, pigs, sheep, goats, dogs, cats, rabbits, guinea pigs, gerbils, hamsters, rats, and mice.

V. THERAPIES

GPR160 antagonists may be applied to treat neuropathic pain related to and including (but not limited to) cancer, chemotherapy-induced neuropathy, diabetic neuropathy, autoimmune neuropathy, and traumatic neuropathy. Additional uses include chronic pain such as rheumatoid arthritis. A therapy will provide relief of one or more symptoms of the disease or disorder, where such relief is either short term, such as with a single administration, or long term, such as with repeated or chronic administration.

GRP160 antagonists will fall into two general categories—biological antagonists and pharmaceutical small molecule antagonists. Biological antagonists include antibodies (directed against GRP160 or CART; commercially available from Pierce, Sigma-Aldrich, Novus Bio, LS Bio, ABCAM and EMD Millipore), peptides (e.g., non-functional fragments of GRP160 and CART) and nucleic acids (siRNA, shRNA, miRNA). Small molecule "drugs" are organopharmaceutical compounds that can be obtained through standard screens of existing chemical libraries.

VI. AGENTS FOR USE IN COMBINATION WITH GPR160 ANTAGONSISTS

Treating pain is a major issue in clinical medicine. A goal of current research is to find ways to improve the efficacy of pain relief using traditional known therapies, and one way is by combining such traditional therapies with the therapies of the present disclosure. In the context of the present disclosure, it is contemplated that an antagonist of GPR160 may be used in a combination therapy with a second agent for treating pain.

The therapies would be provided in a combined amount effective to reduce tolerance and to reduce side effects associated with the opioid, including but not limited to addiction and withdrawal. This process may involve contacting the patient with the agents/therapies at the same time. This may be achieved by contacting the patient with a single composition or pharmacological formulation that includes both agents, or by contacting the patient with two distinct compositions or formulations, at the same time, wherein one composition includes the GPR160 antagonist and the other includes the second agent.

Alternatively, the treatment according to the present disclosure may precede or follow the other treatment by intervals ranging from minutes to weeks. In embodiments where the second drug and the GPR160 antagonist are applied separately to the subject, one would generally ensure that a significant period of time did not expire between each delivery, such that the therapies would still be able to exert an advantageously combined effect on the subject. In such instances, it is contemplated that one would administer both modalities within about 12-24 hours of each other, within about 6-12 hours of each other, or with a delay time of only about 12 hours. In some situations, it may be desirable to extend the time period for treatment significantly; however, where several days (2, 3, 4, 5, 6 or 7) to several weeks (1, 2, 3, 4, 5, 6, 7 or 8) lapse between the respective administrations.

It also is conceivable that more than one administration of either the $A_3AR$ agonist or the opioid therapy will be desired. Various combinations may be employed, where the GPR160 antagonist is "A," and the second therapy is "B," as exemplified below:

| | | | | | |
|---|---|---|---|---|---|
| A/B/A | B/A/B | B/B/A | A/A/B | B/A/A | A/B/B |
| B/B/B/A | B/B/A/B | A/A/B/B | A/B/A/B | A/B/B/A | B/B/A/A |
| B/A/B/A | B/A/A/B | B/B/B/A | A/A/A/B | B/A/A/A | A/B/A/A |
| A/A/B/A | A/B/B/B | B/A/B/B | B/B/A/B | | |

Other combinations, including chronic and continuous dosing of one or both agents, are contemplated.

A. Opioids

Opioids, also known as narcotics, are increasingly recognized as important treatment options for chronic pain. Opioids, along with anticonvulsants and antidepressants are the most consistently effective class of drugs for neuropathic pain. Opioids must be used only in appropriate individuals and under close medical supervision. Several opioids, particularly methadone, and ketobemidone possess NMDA antagonism in addition to their μ-opioid agonist properties. Methadone does so because it is a racemic mixture; only the l-isomer is a potent μ-opioid agonist. The d-isomer does not have opioid agonist action and acts as an NMDA antagonist; d-methadone is analgesic in experimental models of chronic pain. Clinical studies are in progress to test the efficacy of d-methadone in neuropathic pain syndromes.

The following is a non-limiting list of opioids that can be administered in combination with GPR160 antagonists in accordance with the present disclosure: Morphine, Opium, Hydromorphone, Nicomorphine, Oxycodone, Dihydrocodeine, Diamorphine, Papaveretum, Codeine, Phenylpiperidine derivatives, Ketobemidone, Pethidine, Fentanyl, Pethidine, Diphenylpropylamine derivatives, Piritramide, Dextropropoxyphene, Bezitramide, Methadone, Dextropropoxyphene, Benzomorphan derivatives, Pentazocine, Phenazocine, Oripavine derivatives, Buprenorphine, Etorphine, Oripavine derivatives, Morphinan derivatives, Butorphanol, Nalbuphine, Tilidine, Tramadol and Dezocine.

B. Gabapentanoids

Gabapentinoids are 3-substituted derivatives of the neurotransmitter γ-aminobutyric acid (GABA) which selectively block $α_2δ$-containing voltage-dependent calcium channels. Clinically-used gabapentinoids include gabapentin (Neurontin) and pregabalin (Lyrica), as well as a gabapentin prodrug, gabapentin enacarbil (Horizant). Another analogue mirogabalin is in clinical trials but has not yet been approved. Other compounds from this family used in research but not developed for medical use include atagabalin, 4-methylpregabalin and PD-217,014. Gabapentinoids are used clinically in the treatment of conditions including epilepsy, neuropathic pain, fibromyalgia, anxiety, and restless legs syndrome, among others. The OTC (Anglo-sphere) and Russian pharmaceutical nootropic Phenibut, having its origins deriving from Soviet-engineered cosmonaut medicine, and its Vitamin B-modulated cousin, Picamilon, may also said to be "gabapentinoids"—scientifically crossing the blood brain barrier after the manner of this class—despite the international confusion regarding the precise clinical and medicinal usages and interrelated governmental categorizations of these compounds in terms of "liceity."

C. Other Pain Therapies

The following is a discussion of different therapies currently applied against nociceptive pain conditions. Such is exemplary and not limiting. Currently, there are a wide number of agents effective at treating nociceptive pain. These include salicylates, such as Aspirin (acetylsalicylic acid), Diflunisal and Salsalate, Propionic acid derivatives (Ibuprofen, Dexibuprofen, Naproxen, Fenoprofen, Ketoprofen, Dexketoprofen, Flurbiprofen, Oxaprozin, Loxoprofen), Acetic acid derivatives, (Indomethacin, Tolmetin, Sulindac, Etodolac, Ketorolac, Diclofenac, Nabumetone), Enolic acid (Oxicam) derivatives (Piroxicam, Meloxicam, Tenoxicam, Droxicam, Lornoxicam, Isoxicam), Fenamic acid derivatives or "Fenamates" (Mefenamic acid, Meclofenamic acid, Flufenamic acid, Tolfenamic acid), Selective COX-2 inhibitors (Celecoxib, Rofecoxib, Valdecoxib, Parecoxib, Lumiracoxib, Etoricoxib, Firocoxib), Sulphonanilides such as Nimesulide, and a range of other compounds (Licofelone, Lysine clonixinate, Hyperforin, Figwort).

VII. EXAMPLES

The following examples are included to demonstrate particular embodiments of the disclosure. It should be appreciated by those of skill in the art that the techniques disclosed in the examples which follow represent techniques discovered by the inventor to function well in the practice of the disclosure, and thus can be considered to constitute particular modes for its practice. However, those of skill in the art should, in light of the present disclosure, appreciate that many changes can be made in the specific embodiments which are disclosed and still obtain a like or similar result without departing from the spirit and scope of the disclosure.

Example 1

Normal rat dorsal horns were screened for the expression of 38 orphan GPCRs. Twelve of these orphan GPCRs were detected in the rat dorsal horn (FIG. 1): GPR17, GPR18, GPR19, GPR22, GPR30 (not shown), GPR63, GPR83, GPR85, GPR107, GPR160, and GPR183.

Figure 2:
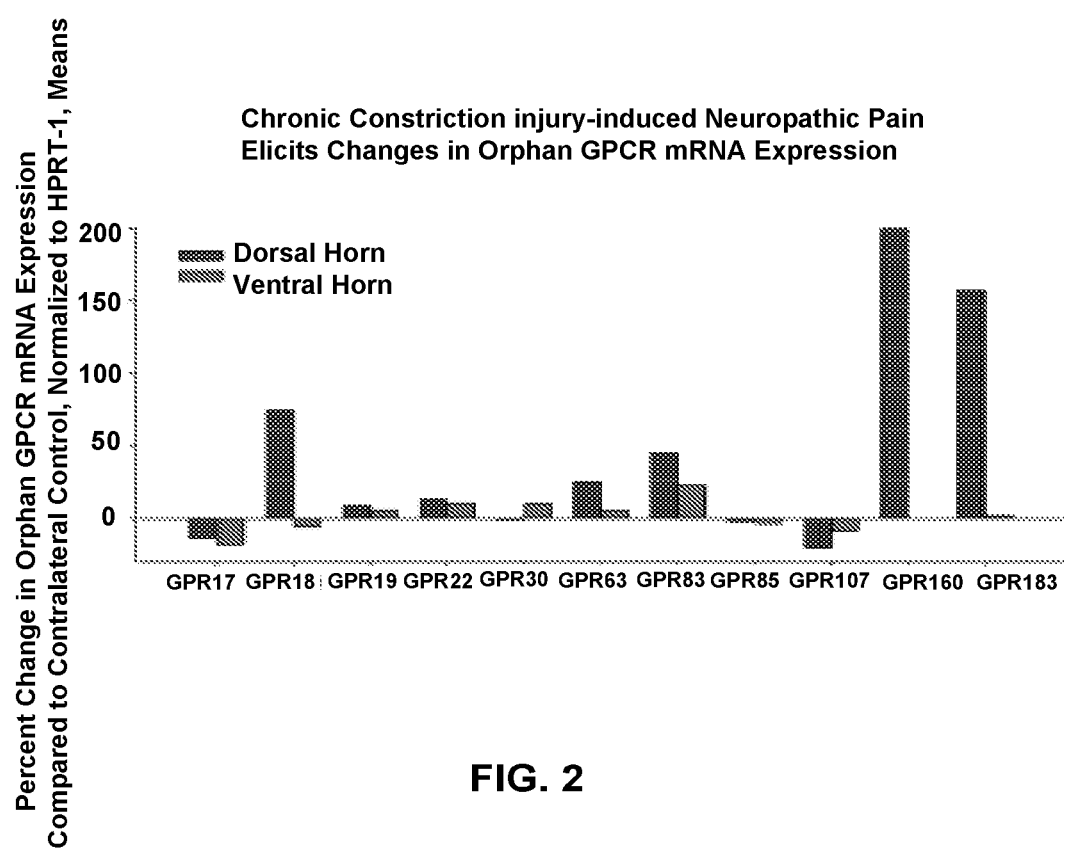
FIG. 2. Expression of Orphan GPCRs in ipsilateral dorsal (left bar of pair) or ventral (right bar of pair) horn compared to contralateral expression in the CCI model.

Two rats then were subjected to chronic constriction injury (CCI), and ipsilateral and contralateral dorsal and ventral horns were removed. Changes in expression of the twelve identified orphan GPCRs were measured using qPCR. Expression of orphan GPCRs was normalized to the housekeeping gene, HPRT-1, and compared to the corresponding tissue on the contralateral (control) side. Expression of three of the orphan receptors, GPR160, GPR183, and GPR18, was elevated greater than 50% in the ipsilateral dorsal horn compared to the contralateral control, with GPR160 exhibiting the greatest increase in expression (~180%) (FIG. 2). No significant changes in expression were observed in the ventral horn.

The inventors decided to focus on GPR160 because of the large induction of GPR160 mRNA in the CCI model. They therefore searched the literature and microarray databases for known tissue expression profiles of GPR160, and found that this receptor is expressed in multiple cancer cell types (Qin et al., 2011; Sheu et al., 2009; Schlomm et al., 2005). They also previously have shown that GPR160 is expressed in hypothalamus, cardiomyocytes, the gastric tumor cell line (KATOIII) pancreatic alpha cells, human embryonic kidney cells (HEK 293), and the human erythroleukemia cell line, TF-1 (Yosten et al., 2012; Yosten et al., 2013). Given this information, the inventors reviewed the literature for ligands with unknown receptors with similar expression profiles to that of GPR160, and identified Cocaine- and Amphetamine-Regulated Transcript (CART) as a potential ligand for GPR160. CART has been implicated in neuropathic pain (Ohsawa et al., 2000; Kozsurek et al., 2007), and can be detected in the dorsal horn (Kozsurek et al., 2007; Kozsurek et al., 2009). In order to determine if GPR160 is necessary for CART signaling, the inventors knocked down expression of GPR160 in KATOIII cells using siRNA (FIG. 3A), then treated GPR160 siRNA-transfected KATOIII cells with CART and evaluated changes in cFos mRNA expression using qPCR. Knockdown of GPR160 completely blocked CART-induced cFos mRNA expression (FIG. 3B), indicating that GPR160 is a good candidate for the CART receptor.

Because many ligands upregulate the expression of their own receptor, the inventors tested the ability of CART to alter GPR160 mRNA expression in KATOIII cells. They found that exposure to CART resulted in an increase in GPR160 mRNA of over 150%, as determined by qPCR (FIG. 4). Experiments currently are underway to determine if CART and GPR160 will co-immunoprecipitate and if the peptide and receptor will co-localize in co-immunoflourescence assays (cells and tissues). These data indicate however that GPR160 is a good candidate for the CART receptor, and, minimally, that GPR160 is necessary for CART signaling in KATOIII cells.

Figure 5:
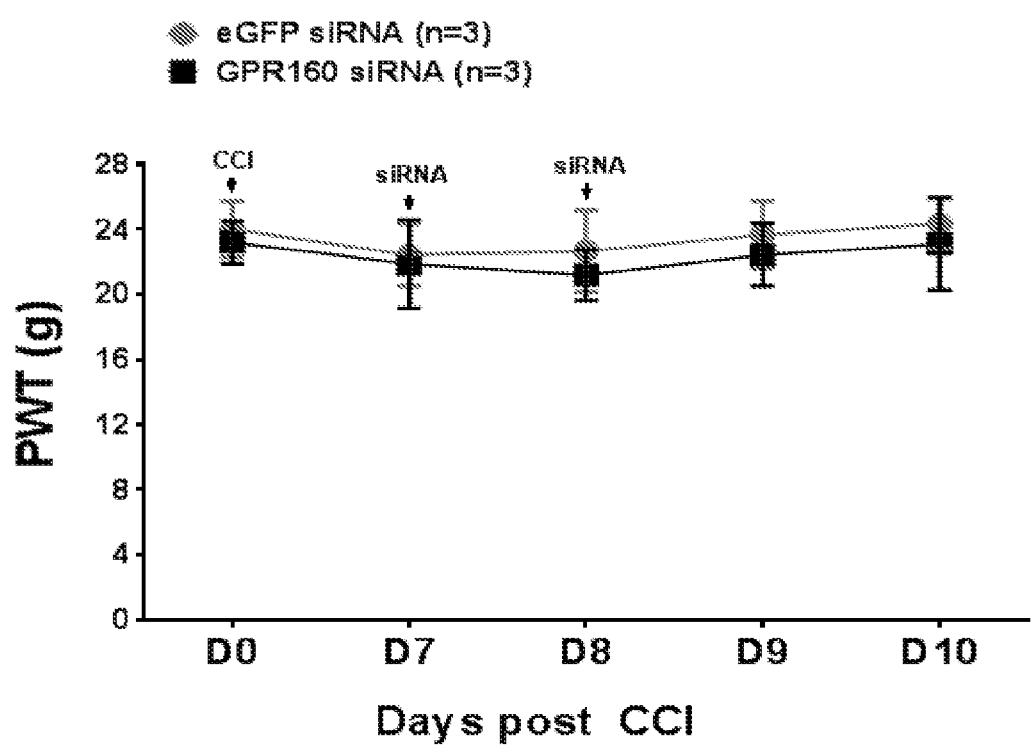
FIG. 5. Knockdown of spinal GPR160 inhibits the development of neuropathic pain due to chronic constriction injury (CCI) of the sciatic nerve in rats. Data represent mean±SD for n=3 rats/group and analyzed by two-way ANOVA with Bonferroni post-hoc tests. # $P<0.01$ vs. D0.
Figure 6:
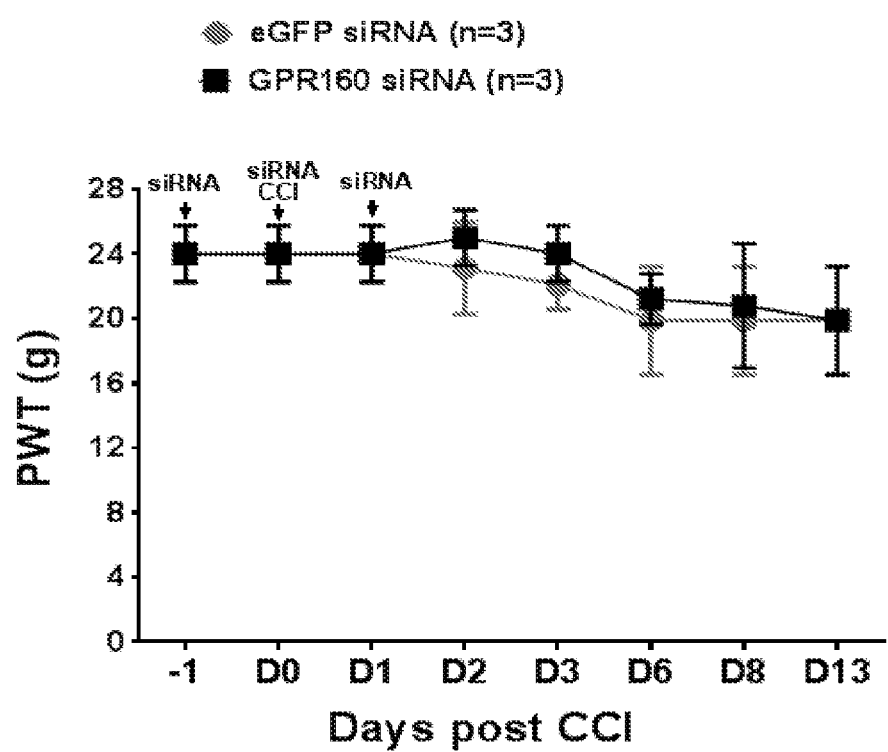
FIG. 6. Knockdown of spinal GPR160 had no effect on non-injured contralateral paw withdrawal thresholds. Data represent mean±SD for n=3 rats/group and analyzed by two-way ANOVA with Bonferroni post-hoc tests. # $P<0.01$ vs. D0.
Figure 7:
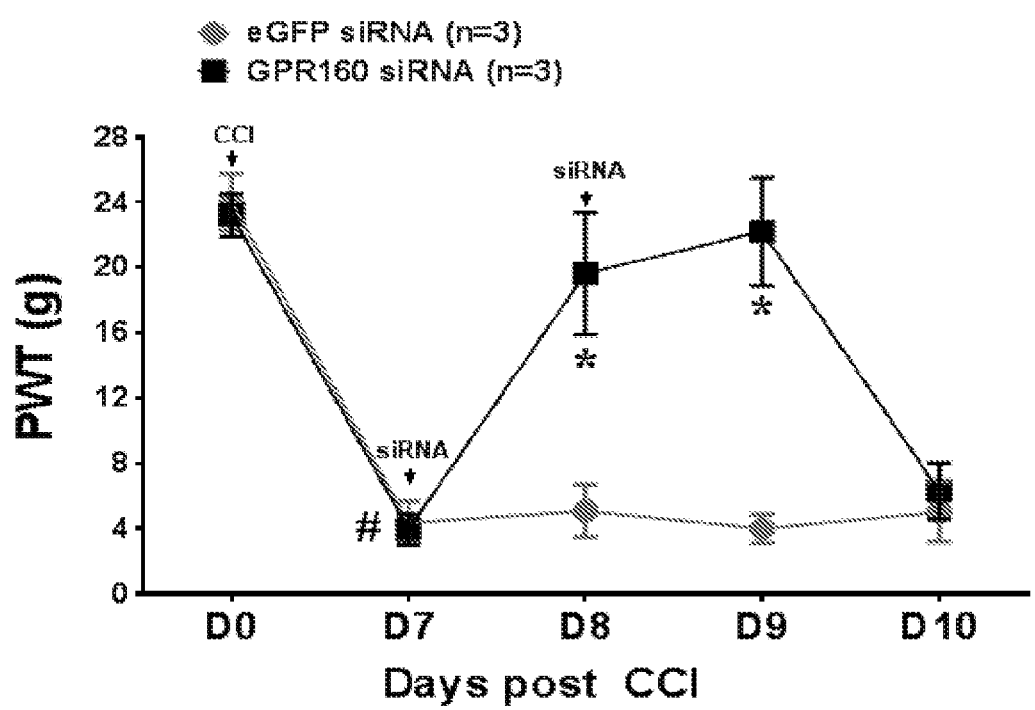
FIG. 7. Knockdown of spinal GPR160 inhibits the development of neuropathic pain due to chronic constriction injury (CCI) of the sciatic nerve in rats. Data represent mean±SD for n=3 rats/group and analyzed by two-way ANOVA with Bonferroni post-hoc tests. # $P<0.01$ vs. D0; *$P<0.01$ vs. D7.
Figure 8:
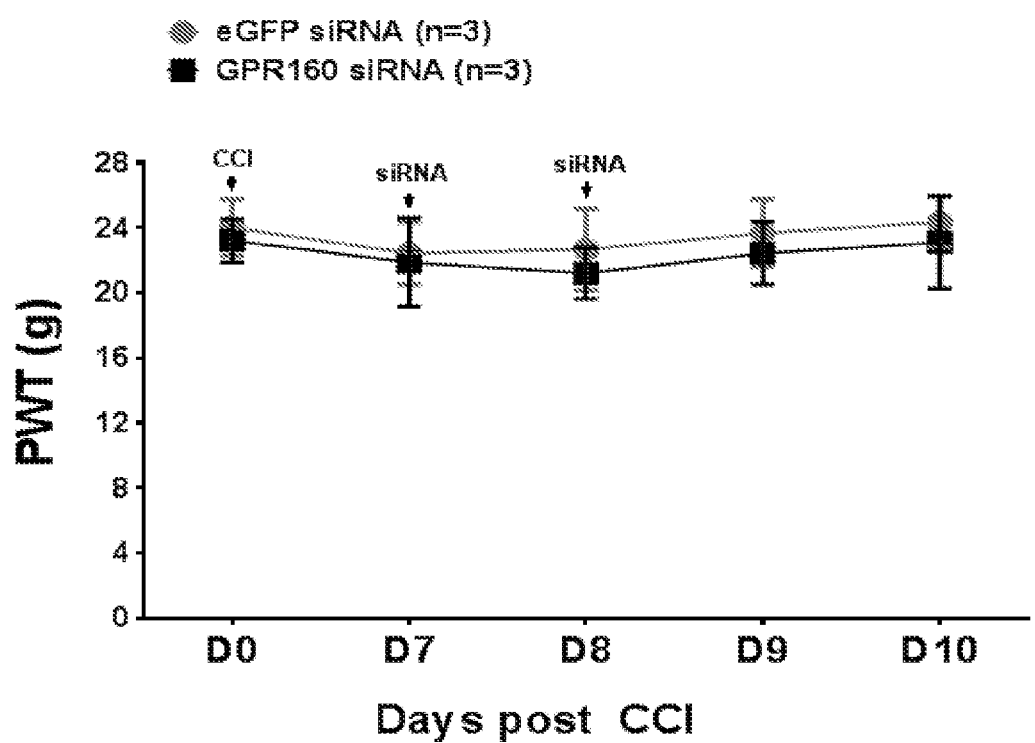
FIG. 8. Knockdown of spinal GPR160 had no effect on non-injured contralateral paw withdrawal thresholds. Data represent mean±SD for n=3 rats/group and analyzed by two-way ANOVA with Bonferroni post-hoc tests. # $P<0.01$ vs. D0; *$P<0.01$ vs. D7.

The inventors next examined whether silencing spinal GPR160 blocks or reverses chronic neuropathic pain. Male Sprague Dawley rats (200-225 g at the start of the experiments) were used for these studies. As shown in FIG. 5, intrathecal (i.th.; Storkson et al., 1996) injection of GPR160 siRNA (2 µg, n=3) but not its negative control eGFP siRNA (2 µg; n=3) blocked the development of neuropathic pain (mechano-allodynia; using the von Frey up and down method, Dixon, 1980) in a well characterized model of constriction injury following ligation of the sciatic nerve (Bennett, G. J. & Xie, 1988). No effects were seen in the contralateral paws (FIG. 6). No observable side effects were noted (i.e., no signs of sedation, lethargy). As shown in FIG. 7, i.th. injection of GPR160 siRNA at time of peak pain (D7) completely reversed mechano-allodynia as measured 24 hours later; a second injection on D8 maintained reversal as tested 24 hours later, stopping i.th. delivery led to a return to baseline values. No effects were seen in the contralateral paws (FIG. 8). No side effects were noted. These results suggest that GPR160 is critical to the induction and maintenance of chronic neuropathic pain states. Note that the X axis depicts days (D) post chronic constriction injury. Noteworthy i.th delivery of GPR160 siRNA (2 µg, n=3) had no effect on acute nociception (tail flick assay; not shown) suggesting that GPR160 does not modulate normal pain signalling.

All of the compositions and/or methods disclosed and claimed herein can be made and executed without undue experimentation in light of the present disclosure. While the compositions and methods of this disclosure have been described in terms of preferred embodiments, it will be apparent to those of skill in the art that variations may be applied to the compositions and/or methods and in the steps or in the sequence of steps of the method described herein without departing from the concept, spirit and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims.

VIII. REFERENCES

The following references, to the extent that they provide exemplary procedural or other details supplementary to those set forth herein, are specifically incorporated herein by reference:

Alexander et al., *Br J Pharmacol.* 170: 1459-1581, 2013.
Bennett & Xie, *Pain* 33, 87-107 1988.

Dixon, W. J., *Annual Rev Pharmacol Toxicol* 20, 441-462, 1980.
Foley, *Anticancer Drugs* 6:Suppl 3, 4-13, 1995.
Kozsurek et al., *Eur J Neurosci.* 29(12):2375-87, 2009; Epub 2009 May 22.
Kozsurek et al., *Eur J Neurosci.* 26(6):1624-31, 2007.
Ohsawa et al., *Eur J Pharmacol.* 399(2-3):165-9, 2000.
Qin et al., *Pigment Cell Melanoma Res.* 24(1):207-18, 2001, Epub 2010 Oct. 21.
Remington's Pharmaceutical Sciences, 15th Edition.
Schlomm et al., *Int J Oncol.* 27(3):713-20, 2005.
Sheu et al., *Cancer Epidemiol Biomarkers Prev.* 18(10): 2709-16, 2009.
Storkson et al., *J Neurosci Methods* 65, 167-172, 1996.
Yosten et al., *J Endocrinol.* 218(2):B1-8, 2013.
Yosten et al., *Am J Physiol Regul Integr Comp Physiol.* 303(9):R941-9, 2012, Epub 2012 Aug. 29.

The invention claimed is:

1. A method of treating pain in a subject comprising administering to said subject an amount of a GPR160 antagonist sufficient to treat pain, wherein the GPR160 antagonist is an antibody that specifically binds to GPR160.

2. The method of claim 1, wherein said subject is a human.

3. The method of claim 1, wherein said subject is a non-human mammal.

4. The method of claim 1, wherein said pain is chronic pain.

5. The method of claim 1, wherein said pain is acute pain.

6. The method of claim 1, wherein said antagonist is administered with a second anti-pain agent.

7. The method of claim 6, wherein said antagonist and said second anti-pain agent are co-formulated.

8. The method of claim 6, wherein said antagonist and said second anti-pain agent are not co-formulated.

9. The method of claim 8, wherein said antagonist and said second anti-pain agent are delivered at distinct times.

10. The method of claim 9, wherein said antagonist is delivered before said second anti-pain agent.

11. The method of claim 9, wherein said antagonist is delivered after said second anti-pain agent.

12. The method of claim 9, wherein said antagonist and said second anti-pain agent are delivered in alternating administrations.

13. The method of claim 6, wherein said second anti-pain agent is an opioid or a gabapentanoid.

14. The method of claim 1, wherein said antagonist is delivered over a period of one week, two weeks, three weeks, four weeks, one month, two months, three months, four months, five months, six months, seven months, eight months, nine months, ten months, eleven months, one year, two years or three years.

15. The method of claim 1, wherein said antagonist is delivered by continuous infusion.

16. The method of claim 15, wherein continuous infusion is provided by an implanted pump.

17. The method of claim 1, wherein said pain is the result of an injury.

18. The method of claim 17, wherein said injury is a penetration wound, a burn, frostbite or a fracture.

19. The method of claim 1, wherein said pain is the result of a disease.

20. The method of claim 19, wherein said disease is diabetes, post-surgical pain, cancer, spinal nerve disease, multiple sclerosis, arthritis, an autoimmune disease, or an infection.

21. The method of claim 1, wherein pain is neuropathic pain.

* * * * *

SEQUENCE LISTING

```
<160> NUMBER OF SEQ ID NOS: 1

<210> SEQ ID NO 1
<211> LENGTH: 116
<212> TYPE: PRT
<213> ORGANISM: Homo sapiens

<400> SEQUENCE: 1

Met Glu Ser Ser Arg Val Arg Leu Leu Pro Leu Leu Gly Ala Ala Leu
1               5                   10                  15

Leu Leu Met Leu Pro Leu Leu Gly Thr Arg Ala Gln Glu Asp Ala Glu
            20                  25                  30

Leu Gln Pro Arg Ala Leu Asp Ile Tyr Ser Ala Val Asp Asp Ala Ser
        35                  40                  45

His Glu Lys Glu Leu Ile Glu Ala Leu Gln Glu Val Leu Lys Lys Leu
    50                  55                  60

Lys Ser Lys Arg Val Pro Ile Tyr Glu Lys Lys Tyr Gly Gln Val Pro
65                  70                  75                  80

Met Cys Asp Ala Gly Glu Gln Cys Ala Val Arg Lys Gly Ala Arg Ile
                85                  90                  95

Gly Lys Leu Cys Asp Cys Pro Arg Gly Thr Ser Cys Asn Ser Phe Leu
            100                 105                 110

Leu Lys Cys Leu
        115
```